United States Patent
Altafi

[19]

[11] Patent Number: 6,112,704
[45] Date of Patent: Sep. 5, 2000

[54] INGUINAL HERNIA SUPPORT

[76] Inventor: Ali A. Altafi, 5770 Rudy Dr., San Jose, Calif. 95124

[21] Appl. No.: 09/357,345

[22] Filed: Jul. 14, 1999

[51] Int. Cl.$^7$ ........................................................ A61F 5/24
[52] U.S. Cl. ............................................ 121/96.1; 602/13
[58] Field of Search .................................... 602/5, 13, 19; 128/95.1, 96.1, 118.1

[56] References Cited

U.S. PATENT DOCUMENTS

| | | | |
|---|---|---|---|
| 4,416,272 | 11/1983 | Nelkin | 128/95.1 |
| 4,559,933 | 12/1985 | Batard | 602/13 |
| 4,703,750 | 11/1987 | Sebastian | 602/13 |
| 5,123,407 | 6/1992 | Dewhurst | 602/13 |
| 5,383,893 | 1/1995 | Daneshvar | 128/118.1 |

*Primary Examiner*—Michael A. Brown
*Attorney, Agent, or Firm*—H. M. Stanley

[57] ABSTRACT

A support for inguinal hernia is disclosed wherein a corset garment having elasticized walls is provided with a pocket or pockets on the inside wall of the portion of the garment that is adjacent the abdomen of a wearer. A plurality of pads are provided for insertion in the pocket or pockets to provide pressure against the underlying inguinal area. The pockets are placed in a location to accommodate the location of a hernia or hernias suffered by a particular user. The number of pads placed in the pocket or pockets is selected to obtain a combined thickness of pads that affords optimum wearer comfort so that the support is thereby customized for the wearer.

3 Claims, 1 Drawing Sheet

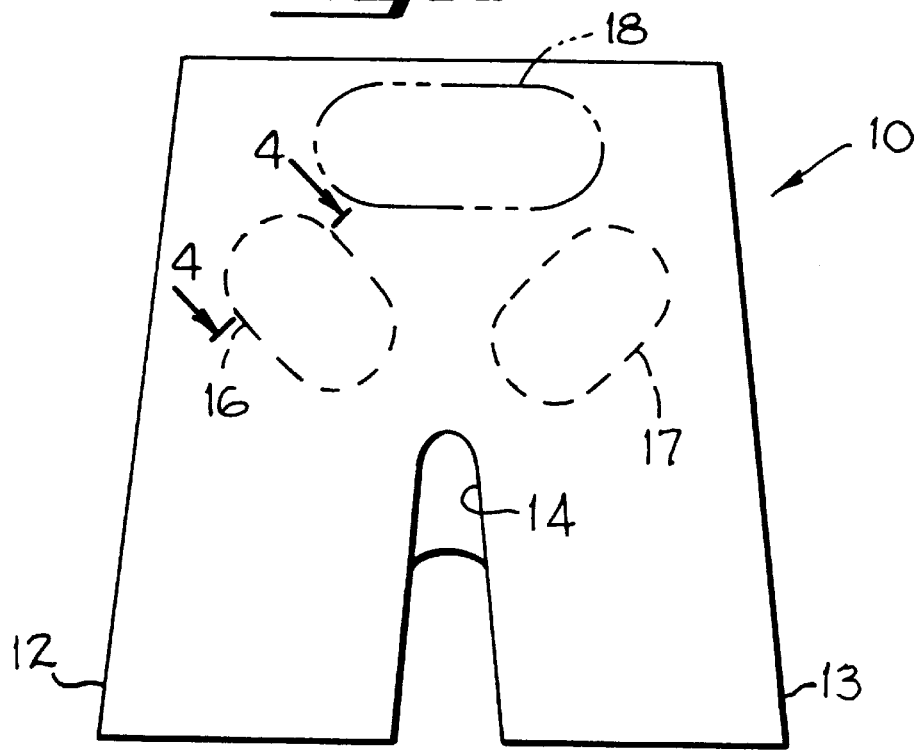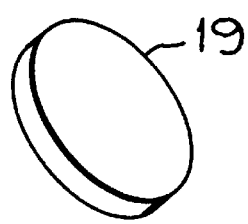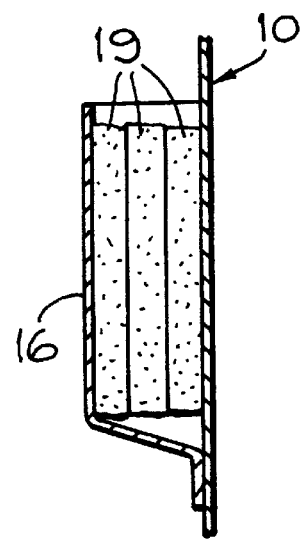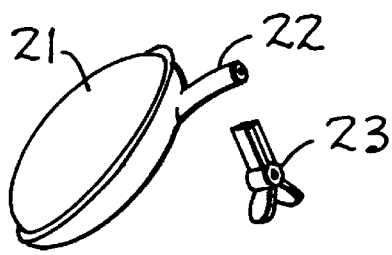

INGUINAL HERNIA SUPPORT

SUMMARY OF THE INVENTION

An adjustable support for a hernia which is located in the inguinal area of a hernia sufferer includes a corset having an inner surface and being configured for wearing about the hips and extending into the inguinal area of the hernia sufferer. At least one pocket is attached to the inner surface in position to overlie the herniated location. A plurality of layers of compliant material, is disposed in the at least one pocket for creating pressure so that the thickness of the plurality of layers is adjustable.

In another aspect of the invention a support for applying pressure in an area of hernia in the inguinal region of a hernia sufferer includes a an adjustable garment configured for wearing about the hips and extending into the inguinal region. The garment has an elasticized wall, which has an inner surface. A pocket is attached to the inner surface overlying the area of the hernia and a plurality of layers of compliant material is placed in the pocket whereby the thickness of the plurality of layers and therefore the pressure against the hernia area is adjustable by adjusting the number of layers.

BRIEF DESCRIPTION OF THE DRAWINGS

FIG. 1 shows an embodiment of the garment of the present invention.

FIG. 2 depicts a pad used in the present invention.

FIG. 3 depicts an inflatable member used in the present invention.

FIG. 4 is a section along the line 4—4 of FIG. 1.

DESCRIPTION OF THE PREFERRED EMBODIMENTS

A hernia is the protrusion of part of an organ into or through an abnormal opening in a containing wall for the organ. The most common type of hernia is the inguinal hernia, which is due to weakness of the lower abdominal wall at its junction with the thigh in the region of the groin. Hernias frequently occur here on both sides in men and women. Commonly, hernias develop because of a congenital weakness or a prolonged or sudden strain without proper support in the region involved. Hernias occur in the middle of the abdomen particularly in women after the abdominal muscles have been weakened from childbirth. Occasionally, hernia develops at a site of weakening in a scar resulting from an invasive operation.

In general, the invention disclosed herein includes a corset-like garment for use by sufferers of inguinal hernia. The garment has elasticized wall portions for surrounding the hips and buttocks of a wearer and extends into the wearer's inguinal area. A pocket or pockets is fastened in any convenient fashion to the inside of the garment in positions overlying the location of the herniated tissue. A pad or combination of pads, of sufficient thickness to provide a comfortable level of pressure to the herniated area is inserted in the pocket (or pockets for multiple hernial areas). Alternatively, an inflatable bag is located in a properly located pocket and inflated to provide the comfortable level of pressure.

FIG. 1 shows a corset-like garment 10 having a waistband 11 and two leg portions 12 and 13 through which the legs of a wearer extend. The garment 10 has an opening 14 in the crotch area thereof so that the wearer may perform normal bodily functions without removing the garment. The area of the garment above the opening 14 and extending to the waistband 11 covers that portion of a wearer which will be referred to as the inguinal area from the wearer's groin area to approximately the height of the wearer's navel. In this inguinal area a first pocket 16 is shown in dashed lines fastened to the inside surface of the corset-like garment as shown. On the opposite side of the front of the garment 10 as seen in FIG. 1, a second pocket 17 is shown in dashed lines representing attachment to the inside surface of the garment 10. An additional pocket 18 is shown in phantom line extending across the upper reaches of the inguinal area just below the waistband 11 and attached to the inside surface of the front of the corset-like garment 10. The point to be made is that the first and second pockets 16 and 17 and/or the additional pocket 18 are positioned on the inside surface of the front of the corset-like garment in a location to overlie a hernia existing in the inguinal area of a wearer. Therefore, the location of the pocket or pockets on the inside surface of the garment 10 may be customized to occupy a position or positions adjacent a hernia location or locations on an individual wearer.

FIG. 2 shows a pad 19, which is a solid pad of a compliant material such as foam rubber, etc. The pockets 16, 17 and 18 of FIG. 1 all have upper openings therein to accept and retain the pads 19. As seen in FIG. 4 a plurality of pads 19 are inserted in the pockets for the purpose of adjusting the pad combination thickness and therefore the pressure exerted against the inguinal region by the combination of pads when the garment 10 is worn by a hernia sufferer.

Alternatively, an inflatable bag 21 is shown in FIG. 3 having an inflation port 22. The inflatable bag 21 is configured to pass through the openings in any of the pockets 16, 17 and 18 and to be inflated therein to a level that provides comfort to the wearer of the garment 10. Any suitable means for sealing the port 22 after inflation of the bag 21 is appropriate such as the clip 23 shown in FIG. 3.

Although the best mode contemplated for carrying out the present invention has been shown and described herein, it will be understood that modification and variation may be made without departing from what is regarded to be the subject matter of the invention.

What is claimed:

1. An adjustable support for a hernia located in the inguinal area of a hernia sufferer, comprising
   a corset having an inner surface and being configured for wearing about the hips and extending into the inguinal area of the hernia sufferer,
   at least one pocket attached to said inner surface in position to overlie the herniated location, and
   a plurality of layers of compliant material disposed in said at least one pocket for creating pressure against the hernia, whereby the thickness of the plurality of layers and therefore the pressure is adjustable.

2. The support of claim 1, wherein the hernia sufferer has multiple inguinal hernias, said at least one pocket comprising
   multiple pockets wherein a pocket overlies each of the multiple inguinal hernias, and
   a plurality of layers of compliant material disposed in each of said multiple pockets.

3. An adjustable support for applying pressure in an area of hernia in the inguinal region of a hernia sufferer, comprising
   a garment configured for wearing about the hips and extending into the inguinal region,
   an elasticized wall in said garment having an inner surface, a pocket attached to said inner surface overlying the area of the hernia, and a plurality of layers of compliant material disposed in said pocket, whereby thickness of said plurality of layers and pressure in the area of hernia is adjustable by adjusting the number of layers.

* * * * *